(12) United States Patent
Yang et al.

(10) Patent No.: US 11,583,658 B2
(45) Date of Patent: Feb. 21, 2023

(54) OUT OF PLANE DEFLECTABLE CATHETERS

(71) Applicant: Medtronic, Inc., Minneapolis, MN (US)

(72) Inventors: Zhongping C. Yang, Woodbury, MN (US); Megan L. Platner, Eden Prairie, MN (US); Kimberly A. Ganzel, Centerville, MN (US); Jay T. Rassat, Buffalo, MN (US); Michael L Freiborg, New Hope, MN (US); Varun Bhatia, Minneapolis, MN (US); Terrell M. Williams, Brooklyn Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 158 days.

(21) Appl. No.: 16/401,397

(22) Filed: May 2, 2019

(65) Prior Publication Data
US 2020/0155798 A1    May 21, 2020

Related U.S. Application Data

(60) Provisional application No. 62/768,196, filed on Nov. 16, 2018.

(51) Int. Cl.
*A61M 25/00* (2006.01)
*A61N 1/05* (2006.01)
*A61M 25/01* (2006.01)

(52) U.S. Cl.
CPC ......... *A61M 25/0041* (2013.01); *A61N 1/056* (2013.01); *A61M 25/0054* (2013.01); *A61M 25/0108* (2013.01); *A61M 25/0147* (2013.01)

(58) Field of Classification Search
CPC .......... A61M 26/0041; A61M 25/0108; A61M 25/0041; A61M 25/0147; A61M 25/0054; A61N 1/056; A61N 1/057; A61N 1/372
See application file for complete search history.

(56) References Cited

U.S. PATENT DOCUMENTS

| 5,256,158 | A  | * | 10/1993 | Tolkoff | A61B 1/012 604/529 |
| 6,926,669 | B1 | * | 8/2005  | Stewart | A61M 25/0147 601/3 |
| 7,647,124 | B2 | * | 1/2010  | Williams | A61M 25/0041 607/122 |

(Continued)

OTHER PUBLICATIONS (PCT/US2019/061163) PCT Notification of Transmittal of the International Search Report and the Written Opinion of the International Searching Authority, dated Mar. 9, 2020, 8 pages.

(Continued)

*Primary Examiner* — Theodore J Stigell
*Assistant Examiner* — Robert F Allen
(74) *Attorney, Agent, or Firm* — Shumaker & Sieffert, P.A.

(57) ABSTRACT

An example catheter includes a handle assembly having a control member, an elongate body, a pull wire, and at least one radiopaque marker. The elongate body defines a lumen configured to receive a medical electrical lead including at least one electrode array. The elongate body includes a proximal portion coupled to the handle assembly and a distal portion that includes an articulating segment and a preformed curve segment. The at least one radiopaque marker is positioned on the distal portion. The pull wire extends from the control member and is anchored to the elongate body distal to the articulating segment such that actuation of the control member controllably bends the articulating segment in a first curve in a first geometric plane. The preformed curve segment defines a second curve in a second geometric plane different from the first geometric plane.

29 Claims, 10 Drawing Sheets

(56) References Cited

U.S. PATENT DOCUMENTS

| | | | |
|---|---|---|---|
| 7,729,782 B2 | 6/2010 | Williams | |
| 8,606,369 B2 | 12/2013 | Williams et al. | |
| 2004/0116993 A1* | 6/2004 | Clemens | A61N 1/056 607/122 |
| 2004/0260241 A1* | 12/2004 | Yamamoto | A61N 1/0575 604/117 |
| 2005/0080470 A1* | 4/2005 | Westlund | A61N 1/0587 607/119 |
| 2007/0112405 A1* | 5/2007 | Williams | A61M 25/0041 607/122 |
| 2012/0232563 A1* | 9/2012 | Williams | A61M 25/0108 606/129 |
| 2015/0094735 A1* | 4/2015 | Ward | A61N 1/056 606/129 |
| 2017/0354427 A1* | 12/2017 | Bonnette | A61B 17/32037 |
| 2018/0168503 A1 | 6/2018 | Waldhauser et al. | |

OTHER PUBLICATIONS

Dandamudi, MD, FHRS, et al., "How to perform permanent His bundle pacing in routine clinical practice," Heart Rhythm, vol. 13, No. 6, Jun. 2016, pp. 1362-1366.

Stephenson, et al., "High resolution 3-Dimensional imaging of the human cardiac conduction system from microanatomy to mathematical modeling," Scientific Reports, published online Aug. 3, 2017, 13 pp.

Vijayaraman, MD, FHRS, et al., "Permanent His bundle pacing: Recommendations from a Multicenter His Bundle Pacing Collaborative Working Group for standardization of definitions, implant measurements, and follow-up," Heart Rhythm, Dec. 2017, 9 pp.

\* cited by examiner

OUT OF PLANE DEFLECTABLE CATHETERS

This application claims the benefit of U.S. Provisional Application No. 62/768,196, entitled "OUT OF PLANE DEFLECTABLE CATHETERS," and filed on Nov. 16, 2018, which is incorporated herein by reference in its entirety.

TECHNICAL FIELD

This disclosure relates to medical devices including elongated members introducible into a body of a patient.

BACKGROUND

Specialized groups of cardiac cells that form the cardiac conduction system control the frequency, pathway of conduction, and rate of propagation of action potentials through the heart, which cause the heart to beat in an efficient manner. This special conduction system includes the sinoatrial node (SA node), the atrial internodal tracts, the atrioventricular node (AV node), the His bundle, and the right and left bundle branches.

The SA node, located at the junction of the superior vena cava and right atrium, normally acts as the natural pacemaker, generating action potentials, which are conducted through the rest of the heart. When normal conduction pathways are intact, an action potential generated in the SA node is conducted through the atria and to the AV node via the atrial internodal tracts. The conduction through the AV nodal tissue takes longer than through the atrial tissue, resulting in a delay between atrial contraction and the start of ventricular contraction.

The AV node, located in the central fibrous body, conducts the action potential to the His bundle, located above the annulus of the tricuspid valve at the crest of the ventricular muscular septum. The His bundle splits into the left and right bundle branches, which conduct the action potential to specialized fibers called "Purkinje fibers." The bundle branches rapidly conduct the action potential down the ventricular septum, where the high conduction velocity Purkinje fibers activate contractile myocardium, producing choreographed, natural physiological ventricular activation.

Conduction abnormalities may cause slowed or disrupted conduction anywhere along this conduction pathway. For example, the SA node may not generate action potentials at a fast enough rate resulting in too slow of heart rate, or bradycardia. AV block may prevent conduction of the action potential from the atria to the ventricles. A left and right bundle branch block, or other conduction abnormalities in the Purkinje fibers or ventricular myocardium, may cause the contraction of the right and left ventricles to be asynchronous. These and other conduction abnormalities may be treated by an external or implantable pacemaker.

Pacemakers are typically coupled to the heart via one or more implantable medical electrical leads, each carrying one or more electrodes for stimulating the heart and for sensing the intrinsic electrical signals associated with a conducted action potential. Electrodes are commonly placed on the endocardial surface using a transvenous approach. For example, a right ventricular lead may be advanced into the right ventricle and placed such that an electrode is positioned at or near the right ventricular apex. Low capture thresholds and stable lead positioning have made the right ventricular apex a preferred ventricular stimulation site.

However, ventricular pacing at the location of the right ventricular apex does not produce physiological ventricular activation. Both experimental and equivocal clinical studies have shown that septal pacing can improve various indices of cardiac function compared to apical pacing. Direct myocardial stimulation, as occurs in apical pacing, can cause remodeling of the ventricular myocardium, including myofibrillar disarray and local hypertrophy away from the electrode.

The most normal physiological approach to pacing the ventricles when normal AV nodal conduction fails may be to deliver electrical stimulation pulses directly to the His bundle. Depolarization of the His bundle tissue may be conducted normally through the ventricular conduction pathway, down the left and right bundle branches and to the remainder of the ventricular myocardium. The resulting ventricular contraction, which is more rapid and results in a narrow QRS complex and a more vigorous, normal contraction, may produce a better-coordinated ventricular contraction for achieving efficient heart pumping action.

Medical catheters may be advanced into vasculature of a patient to provide a lumen through which a medical device, such as a medical electrical lead, or therapeutic agent may be introduced to a treatment site. Medical catheters may be advanced to the treatment site by a clinician applying an axial force to a portion of the catheter that is outside a body of the patient. Some medical electrical leads may be configured for endocardial introduction into different chambers of a patient's heart, such as the right atrium or right ventricle, using such catheters.

SUMMARY

In general, the disclosure is directed to a catheter configured to facilitate identification of a target location for implantation of a medical electrical lead, and implantation of the medical electrical lead at the target location, as well as methods for using the catheter to identify the target location and implant a medical electrical lead at the target location. As one example, a catheter may facilitate delivering a medical electrical lead to a target location proximate the His bundle for His bundle pacing. The catheter may include a distal portion that is deflectable in three-dimensions, e.g., such that there are curves in two different geometric planes, one or more radiopaque markers on each of the geometric planes, and/or, in some examples, at least one electrode array to map the His bundle. The at least one radiopaque marker and/or at least one electrode array may be used to determine a target implantation location, such as, for example, a target stimulation location. Once the target location is determined, a medical electrical lead may be advanced through a lumen of the catheter to the target location.

In some examples, a catheter may include a handle assembly having a control member; an elongate body extending from a proximal end to a distal end and defining a lumen extending longitudinally within the elongate body, the lumen configured to receive a medical electrical lead including at least one electrode, where the elongate body comprises: a proximal portion coupled to the handle assembly and extending along a longitudinal axis; and a distal portion may include an articulating segment; and a preformed curve segment distal the articulating segment; a pull wire extending from the control member and anchored to the elongate body distal to the articulating segment; and at least one radiopaque marker, where the pull wire, by actuation of the control member, is configured to controllably bend the articulating segment in a first curve in a first geometric plane, and where the preformed curve segment defines a second curve in a second geometric plane different from the first geometric plane, where the at least one radiopaque marker is positioned on the second curve.

In some examples, a delivery catheter may include a handle assembly having a control member; an elongate body extending from a proximal end to a distal end and defining a lumen extending longitudinally within the elongate body, the lumen configured to receive the medical electrical lead, where the elongate body comprises: a proximal portion coupled to the handle assembly and extending along a longitudinal axis; and a distal portion may include an articulating segment; and a preformed curve segment distal the articulating segment, a pull wire extending from the control member and anchored to the elongate body distal to the articulating segment; at least one electrode array configured to sense an electrical signal indicative of a His bundle of a heart of a patient; a first radiopaque marker on the articulating segment; and a second radiopaque marker distal to the articulating segment; where the pull wire, by actuation of the control member, is configured to controllably bend the articulating segment in a first curve in a first geometric plane, and where the preformed curve segment defines a second curve in a second geometric plane different from the first geometric plane, and where an offset of the first geometric plane relative to the second geometric plane is within a range from about 40 degrees to about 50 degrees.

In some examples, a kit may include a catheter including a handle assembly having a control member; an elongate body extending from a proximal end to a distal end and defining a lumen extending longitudinally within the elongate body, where the elongate body comprises: a proximal portion coupled to the handle assembly and extending along a longitudinal axis; and a distal portion may include an articulating segment; and a preformed curve segment distal the articulating segment, a pull wire extending from the control member and anchored to the elongate body distal to the articulating segment; and at least one radiopaque marker positioned on the distal portion, where the pull wire, by actuation of the control member, is configured to controllably bend the articulating segment in a first curve in a first geometric plane, and where the preformed curve segment defines a second curve in a second geometric plane different from the first geometric plane; and an implantable element for at least one of therapy delivery or sensing that is sized for delivery through the lumen and out of the distal end of the elongate body.

In some examples, a method may include advancing a catheter toward a target location within a patient, where the catheter comprises: at least one electrode array configured to detect an electrical signal indicative of the His bundle of a heart of the patient; a handle assembly having a control member; an elongate body extending from a proximal end to a distal end and defining a lumen extending longitudinally within the elongate body, the lumen configured to receive a medical electrical lead, where the elongate body comprises: proximal portion coupled to the handle assembly and extending along a longitudinal axis; and a distal portion may include an articulating segment; and a preformed curve segment distal the articulating segment, a pull wire extending from the control member and anchored to the elongate body distal to the articulating segment; and at least one radiopaque marker positioned on the distal portion, where the pull wire, by actuation of the control member, is configured to controllably bend the articulating segment in a first curve in a first geometric plane, and where the preformed curve segment defines a second curve in a second geometric plane different from the first geometric plane, identifying the target location based on the detection of the electrical signal with the at least one electrode array; and advancing a medical electrical lead through the lumen and out the distal end of the elongate body to the target location.

In some examples, a method may include forming an elongate body extending from a proximal end to a distal end and defining a lumen extending longitudinally within the elongate body, the lumen configured to receive a medical electrical lead including at least one electrode array, where the elongate body comprises: a proximal portion coupled to the handle assembly and extending along a longitudinal axis; and a distal portion may include an articulating segment; and a preformed curve segment distal the articulating segment anchoring a distal end of a pull wire to the elongate body, where the pull wire extends from a control member of a handle assembly to the distal end, where the pull wire, by actuation of the control member, is configured to controllably bend the articulating segment in a first curve in a first geometric plane; positioning at least one radiopaque marker on the distal portion, where the preformed curve segment defines a second curve in a second geometric plane different from the first geometric plane.

The details of one or more examples are set forth in the accompanying drawings and the description below. Other features, objects, and advantages will be apparent from the description and drawings, and from the claims.

DETAILED DESCRIPTION

Figure 1A:
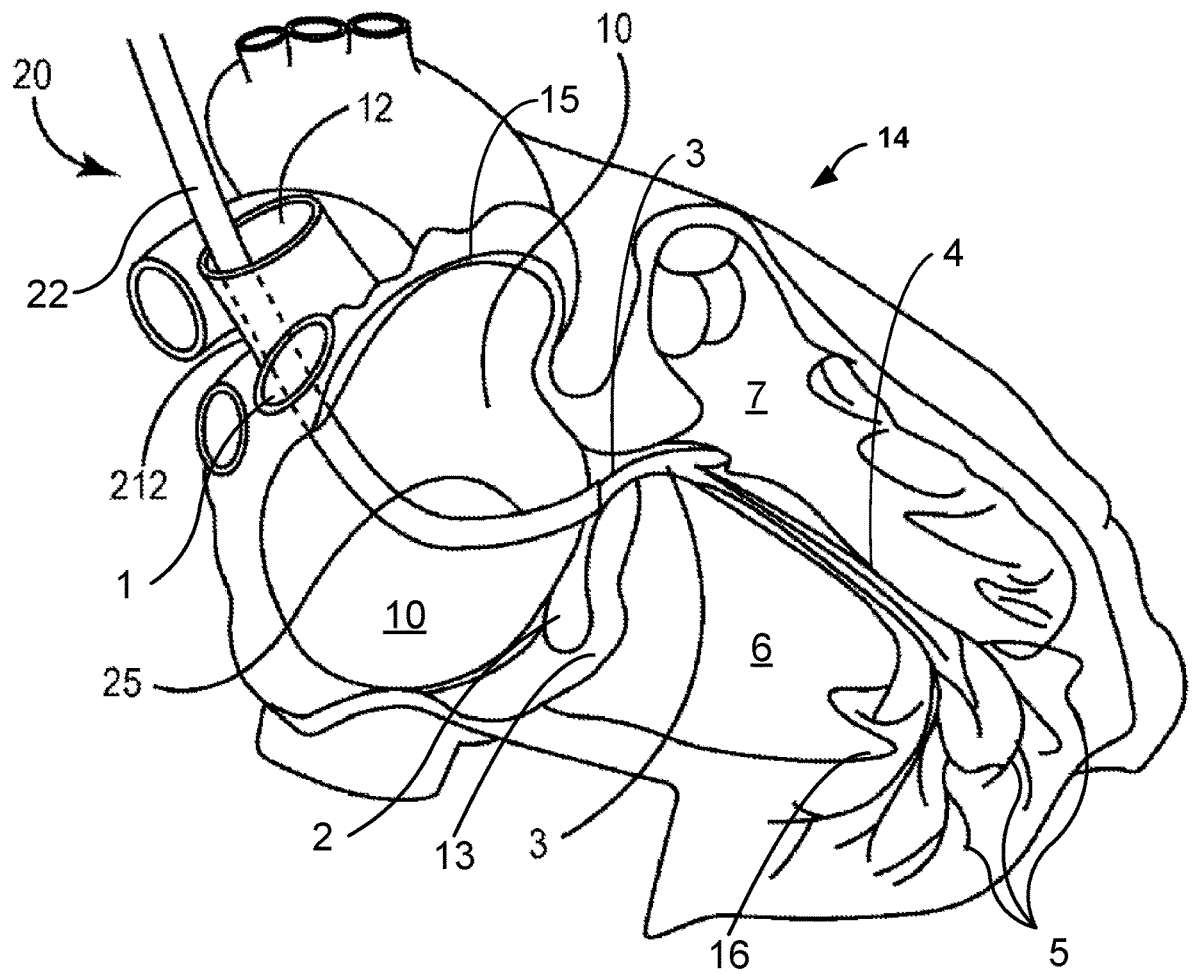
FIG. 1A is a conceptual diagram illustrating a right side of a heart in which a distal portion of an example catheter is positioned.

In general, the disclosure describes example systems, devices, and techniques for implanting medical devices at a target location within a patient. In general, the patient may be a human patient. However, in other examples, the patient may be a non-human patient. The target location may generally include any site within the patient where stimulation, sensing, or drug delivery is desired. In some examples, the target location includes a His bundle, a coronary vein, or tissue suitable for pacing, which is not dead, damaged, or otherwise not operating within general anatomical norms. His bundle pacing may better simulate natural cardiac rhythm compared to pacing at other portions of the heart. However, implant of a medical electrical lead at the His bundle may be difficult.

An example system may include a catheter having features that control the orientation of a distal portion of the catheter. For example, the catheter may include an articulating segment and a preformed curve segment to enable deflection in three-dimensions along two different geometric planes. In some examples, a curve of the articulating segment may be controllable by, for example, a control member coupled to one or more pull wires. In some examples, a curve of the preformed curve segment may be in a first plane offset from a second plane of the curve of the articulating segment, such that the position of the distal tip of the catheter may be controlled in a three-dimensional space.

The catheter also may include features that facilitate identification of the target location and tracking of the distal portion of the catheter relative to the target location. For example, the catheter may include at least one radiopaque marker to facilitate fluoroscopic or other visualization of the catheter, e.g., for steering and/or orienting the catheter, as it is being delivered to the target tissue site. In some examples, the catheter may include at least one electrode array for sensing a waveform, such as an ECG. The target location, such as the His bundle, may be determined based on visualization of the catheter using the at least one radiopaque marker, detection of a characteristic of the waveform using the at least one electrode array, or both. In this way, the example system may make His bundle medical electrical lead implant easier and more predictable, reduce the duration of His bundle medical electrical lead implant procedure, reduce consumption of hospital resources, and/or reduce patient exposure to radiation, compared to other medical electrical lead implant systems.

In this disclosure, the example systems, devices, and techniques will be described with reference to delivering a medical electrical lead to a location proximate a His bundle in a heart. However, it will be understood that example systems, devices, and techniques of the present disclosure are not limited to delivering medical electrical leads to a His bundle. For example, example systems, devices, and techniques described herein may be used to deliver medical electrical leads to a coronary vein, to epicardial tissue, or other locations. Additionally, example systems, devices, and techniques described herein may be used to deliver medical electrical leads for neurostimulation therapy (e.g., spinal cord stimulation), deep brain stimulation, stimulation of one or more muscles, muscle groups or organs, and, generally, stimulation of tissue of a patient. Further, in some examples the example systems, devices, and techniques described herein can be used to deliver catheters for dispensing a drug or other beneficial agent from an implanted or external drug delivery device. In short, the example systems, devices, and techniques described herein can find useful application in delivery of a wide variety of medical electrical leads or catheters for delivery of therapy to a patient or patient sensing.

FIG. 1A is a conceptual diagram illustrating a right side of a heart 14 in which a distal portion 22 of an example catheter 20 is positioned. As illustrated in FIG. 1A, heart 14 has an anterior-lateral wall peeled back to present a portion of the intrinsic conduction system of heart 14 and chambers of a right atrium (RA) 10 and a right ventricle (RV) 6. Pertinent elements of the intrinsic conduction system of heart 14 may include a sinoatrial (SA) node 1, an atrioventricular (AV) node 2, a His bundle 3, a right bundle branch 4, and Purkinje fibers 5. SA node 1 is shown near the superior vena cava (SVC) 12 in the RA 10. An electrical impulse starting at the SA node 1 travels rapidly through tissue of RA 10 and tissue of a left atrium (not shown) to AV node 2. At AV node 2, the impulse slows to create a delay before passing on through His bundle 3, which branches, in an interventricular septum 7, into a right bundle branch 4 and a left bundle branch (not shown) and then, near RV apex 16, into Purkinje fibers 5. Flow of the electrical impulse creates an orderly sequence of atrial and ventricular contraction and relaxation to efficiently pump blood through heart 14.

Due to disease, injury, or natural defects, the intrinsic conduction system of heart 14 may no longer operate within general anatomical norms. Consequently, a cardiac pacemaker system can be implanted into a patient such that electrodes carried by an implantable medical electrical lead are placed in an atrial appendage 15. The electrodes stimulate RA 10 downstream of SA node 1 and the stimulating pulse travels on to AV node 2, His bundle 3, and Purkinje fibers 5 to restore physiological contraction of the heart. However, if a patient has a defective AV node 2 pacing in atrial appendage 15 will not be effective, since the pacing site is upstream of AV node 2, e.g., atrioventricular block. Such a patient may have a cardiac pacemaker system implanted such that medical electrical leads are placed in an RV apex 16. RV apex 16 has been an accepted site for pacing since it is a relatively easy to engage medical electrical leads at this site, and pacing from this site has been demonstrated safe and effective. Due to questions raised by recent studies looking into long-term effects of pacing from RV apex 16, as previously described, there is a great deal of interest in more physiologically correct pacing.

One site for more physiologically correct pacing is the His bundle 3. As described above, the His bundle 3 forms part of the intrinsic conduction system of heart 14, and any pacing applied from the His bundle 3 will conduct through the His bundle 3 to the Purkinje fibers 5 and throughout the RV 6 and left ventricle (not shown). However, determining the location of the His bundle 3 and attaching a medical electrical lead proximate to the His bundle 3 may be difficult.

For example, one preferred location from which the His bundle 3 may be paced is on the atrial aspect of the tricuspid valve annulus, proximal to the anterior attachment of the septal leaflet of valve 13. This location may be accessed from RA 10, and may be difficult to reach using a distal port catheter. Further, once this location is reached, it may be challenging to maintain a distal port catheter in position as the medical electrical lead is fixed to the His bundle 3 or tissue proximate the His bundle 3. Additionally, locating the His bundle 3 may be difficult in at least some hearts, because the His bundle 3 may not be reliably locatable in some patients using imaging techniques.

As illustrated in FIG. 1A, a distal portion 22 of a catheter 20 is positioned within heart 14. A length of catheter 20 may vary, but may be between about 30 and 100 centimeters, with an outer diameter of less than about 14 French, or about 4.667 millimeters. In some examples, catheter 20 may be inserted into heart 14 using a transvenous approach through the SVC 12 into the RA 10 and distal portion 22 may be positioned near a junction between SVC 12 and RA 10 so that a distal end 25 of the catheter is directed into contact with endocardial tissue proximate His bundle 3. In other examples, catheter 20 may be directed through the tricuspid valve 13 to RV 6 and directed into contact with endocardial tissue distal to His bundle 3.

In some examples, catheter 20 is a steerable catheter. In some examples, catheter 20 is a guidable catheter and includes a lumen for receiving a guide wire to assist with advancing the catheter 20 at least a portion of a distance to a target position within heart 14. In some examples, catheter 20 includes features that allow it to effectively transfer force applied to a proximal end, e.g., via a handle assembly (not shown), of catheter 20 into motion of a distal end 25 of catheter 20. For example, distal portion 22 may include multiple curves proximate distal end 25 to facilitate guiding distal end 25 to a target location, such as tissue proximate His bundle 3. In some examples, the multiple curves may be formed by an articulating segment adjustable by, for example, a pull wire that can be manipulated by a control member at the handle assembly, a preformed curve segment, or other features configured to shape a length of distal portion 22.

Catheter 20 may be flexible to facilitate advancement of the catheter 20 through the circulatory system (including SVC 12). For example, catheter 20 may comprise a flexible, biocompatible material such as, for example, silicone or polyurethane. Upon advancing into RA 10, catheter 20 may begin to regain its preformed curve segment.

Figure 1B:
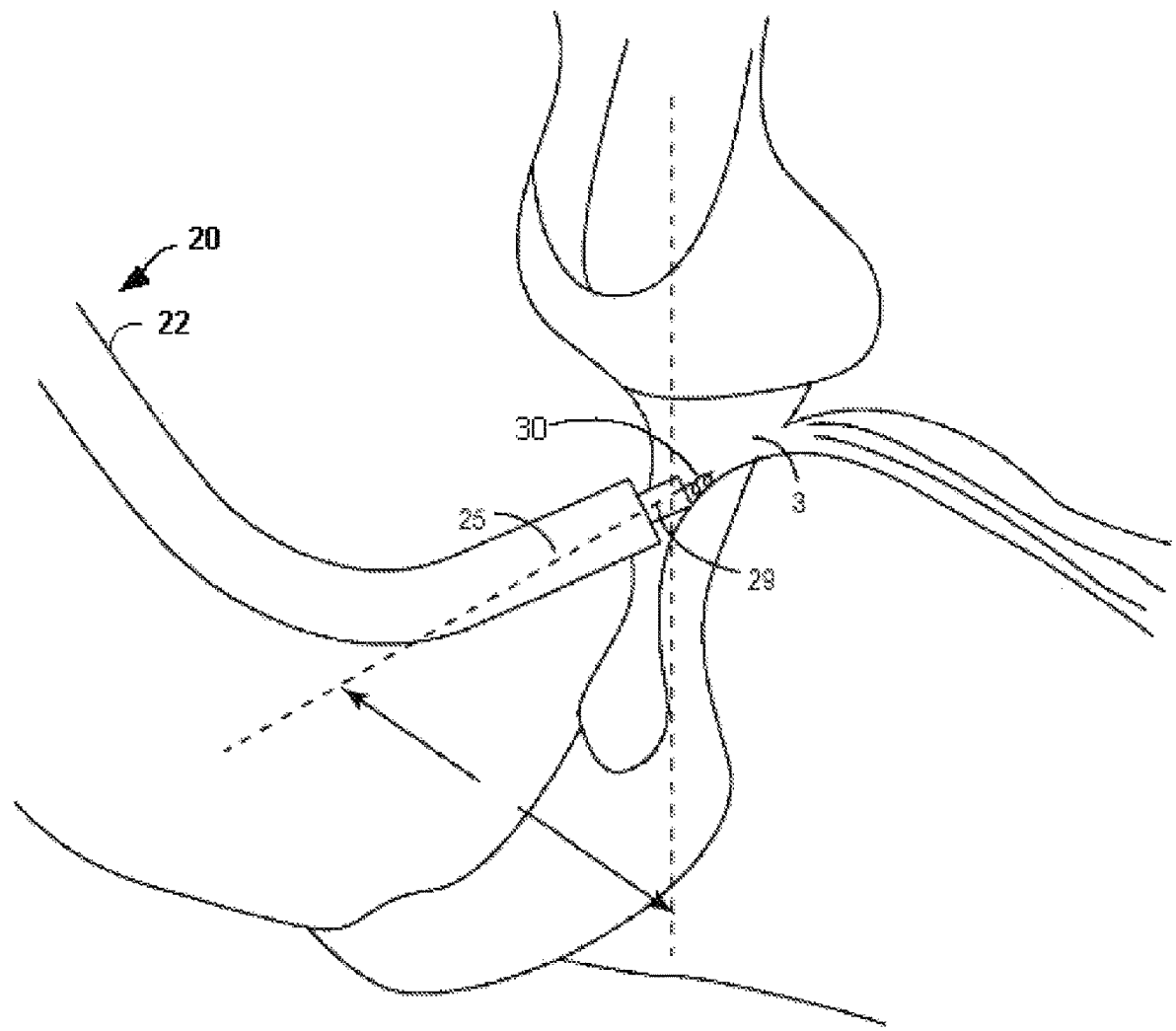
FIG. 1B is an enlarged view of the distal end of the catheter illustrated in FIG. 1A.

FIG. 1B is an enlarged view of a portion of the schematic diagram of FIG. 1A in which a medical electrical lead 29 having a distal helix 30 is extending out of distal end 25 of catheter 20. For example, catheter 20 may include a delivery catheter to delivery medical electrical lead 29. Medical electrical lead 29 is configured to provide physiological pacing. For example, medical electrical lead 29 may provide pacing of heart 14 via electrical pulse delivered to His bundle 3. Distal helix 30 may be configured to anchor medical electrical lead 29 to tissue proximate His bundle 3. For example, during medical electrical lead 29 delivery, a clinician may control distal helix 30, e.g., via a lead body of medical electrical lead 29 controllable at or near a handle assembly of catheter 20, to screw distal helix 30 into the tissue proximate His bundle 3. Although illustrated as distal helix 30, in some examples, catheter 20 may include additional or alternative fixation elements, including, but not limited to, one or more tines or one or more barbs. In some examples, wall 212 of SVC 12 (as illustrated in FIG. 1A) may provide support for distal portion 22 as the operator maneuvers distal end 25 into a proper orientation and advances medical electrical lead 29 distally through a lumen of catheter 20 and out distal end 25. Wall 212 of SVC 12 may provide a more stable support for distal portion 20 than a heart wall, for example, not moving as much as a wall of atrium 10 would with each beat of heart 14. In some examples, distal portion 22 may be sufficiently stiff to enable medical electrical lead 29 to be advanced out of distal end 25 and anchored to tissue proximate to His bundle 3 without support from wall 212 or other portions of heart 14 opposite His bundle 3. In this way, distal portion 22 may not contact an atrial wall or a ventricular wall of heart 14 during positioning of catheter 20 and delivery of medical electrical lead 29 to reduce motion induced by the beating of heart 14 that may otherwise frustrate accurate placement of medical electrical lead 29.

Figure 2A:
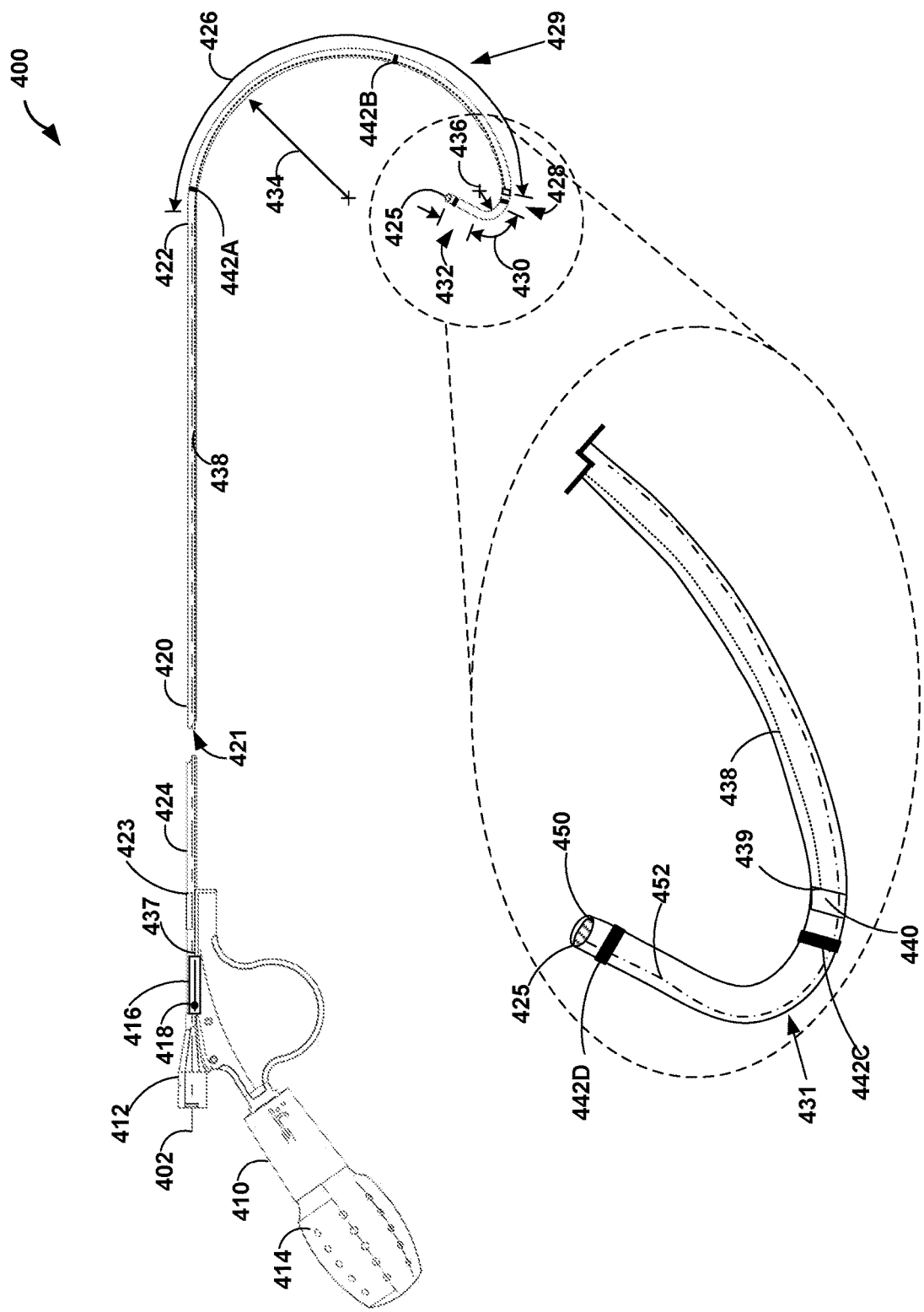
FIGS. 2A-2C are conceptual diagrams illustrating an example catheter, which includes an elongate body and a handle assembly.
Figure 2B:
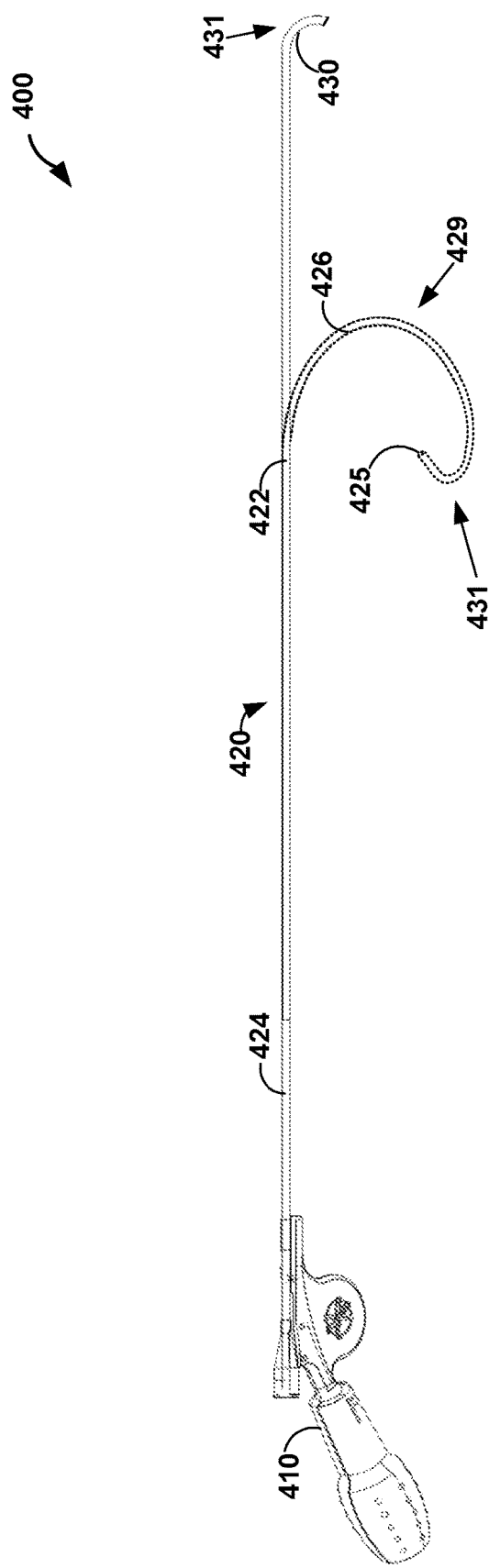
Figure 2C:
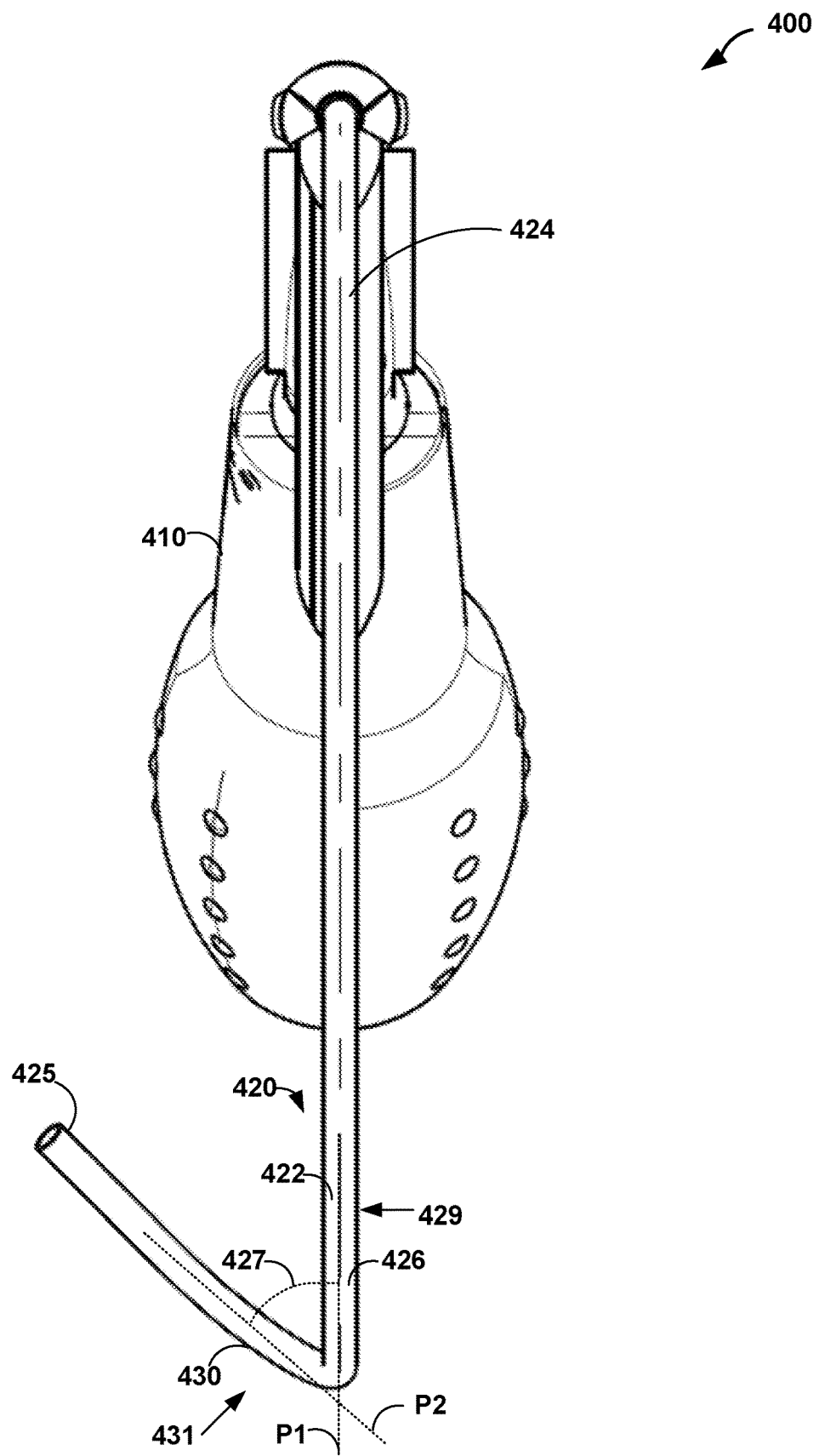

Certain shapes of the articulating segment and/or the preformed curve segment of distal portion 22 may cooperate with anatomy of heart 14 to assist the clinician in positioning catheter 20 and delivering medical electrical lead 29 to tissue proximate His bundle 3. FIGS. 2A-2C are conceptual diagrams illustrating an example catheter 400 including a handle assembly 410 and an elongate body 420. Catheter 400 may be the same as or substantially similar to catheter 20 discussed above in reference to FIGS. 1A and 1B.

Elongate body 420 extends from a proximal end 423 to a distal end 425. Elongate body 420 may include any suitable length to reach the target location of the heart from an access site, such as a femoral access site or a radial access site. In some examples, elongate body may be in a range between about 30 centimeters (cm) and about 100 cm. Elongate body 420 may define a lumen 421 extending longitudinally within elongate body 420. Lumen 421 may be configured to receive a medical electrical lead that includes at least one electrode array. For example, lumen 421 may be sized to pass a medical electrical lead through an entire length of lumen 421. In some examples, elongate body 420 may include a plurality of lumens, each lumen extending along and/or parallel to longitudinal axis 402.

Elongate body 420 may include proximal portion 424 and distal portion 422. Elongate body 420 has a flexibility allowing deflection of proximal portion 424 and/or distal portion 422 when elongate body 420 is maneuvered within the vasculature of a patient. Proximal portion 424 may be coupled to handle assembly 410 having a control member 416. Proximal portion 424 extends along longitudinal axis 402. In some examples, proximal portion 424 may include a stabilizing sheath that surrounds proximal portion 424 and is configured to transfer force, such as torque, at handle assembly 410 to distal portion 422. In some examples, control member 416 may include one or more controls 418 that are coupled to pull wire 438. One or more controls 418 may be manipulated to control a length of pull wire 438 extending through elongate body 420. In some examples, handle assembly 410 may include a hub 412. Hub 412 may be configured to provide access to a lumen of elongate body 420. In some examples, handle assembly 410 may include an adjustable handle 414. Adjustable handle 414 may be configured to manipulate, e.g., rotate, the deflection of distal portion 422. In some examples, handle assembly 410 may include a flushing assembly configured to couple to a syringe to, for example, purge air from lumens of catheter 400.

Distal portion 422 includes, as discussed above, an articulating segment 426 and a preformed curve segment 430 distal to articulating segment 426. In some examples, a shape of distal portion 422 may be controllable. For example, pull wire 438, e.g., by actuation of control member 416, may be configured to controllably bend articulating segment 426 in a first curve 429 in a first geometric plane P1. The first geometric plane is illustrated in the plane of the page in FIGS. 2A and 2B, and as plane P1 in FIG. 2C. In some examples, the amount of actuation of control member 416 may control the degree of curvature of articulating segment 426. For example, a degree of curvature of articulating segment 426 may be controlled in a range between about 0 degrees to about 240 degree, such as between about 45 degrees and about 180 degrees or between about 85 degrees and about 100 degrees. In some examples, a length of articulating segment 426 defining first curve 429 may be within a range from about 5 cm to about 20 cm, such as from about 12 cm to about 15 cm. In some examples, a radius 434 of first curve 429, when articulated, may be within a range between about 5 mm and about 60 mm, such as between about 10 mm and about 30 mm or between about 15 mm and about 20 mm. By controlling the degree of curvature, articulating segment 426 may enable first curve 429 to be adjusted to accommodate a variation in the position of His bundle 3 or a difference in size of a dilated heart compared to an average sized heart.

Pull wire 438 may enable control of the degree of curvature of articulating segment 426 from handle assembly 410. For example, a proximal end 437 of pull wire 438 may be coupled to control member 416. Pull wire 438 may extend from control member 416 to a distal end 439 of pull wire 438 anchored to elongate body 420 distal to articulating segment 426. For example, distal end 439 may be anchored to elongate body 420 using a pull band 440. Pull band 440 may include any suitable structure configured to anchor a distal end 439 of pull wire 438 to elongate body 420 distal articulating segment 426. In some examples, pull band 440 may include a radiopaque marker, gold, platinum iridium, other noble metals or alloys thereof, stainless steel, other materials configured to withstand deflection force from actuating pull wire 438 which may include sputtered noble metals, or combinations thereof. In some examples, pull wire 438 includes a single pull wire. In other example, pull wire 438 may include a plurality of pull wires. In examples in which pull wire 438 include a plurality of pull wires, each pull wire of the plurality of pull wires may be configured to control a deflection of distal portion 422 in one or more directions. Pull wire 438 may include any suitable material and construction. In some examples, pull wire 438 may have a diameter of approximately 0.009 inch (0.23 mm) and may be formed from medical grade 304 stainless steel. In some examples, pull wire 438 may include a coating, e.g., a fluoropolymer, such as polytetrafluoroethylene (PTFE). By anchoring distal end 439 of pull wire 438, actuation of control member 416 in a proximal direction, e.g., to shorten a length of pull wire 438 extending through elongate body, may result in a controllable bending of articulating segment 426 in first geometric plane P1. Actuation of control member 416 in a distal direction, e.g., to lengthen a length of pull wire 438, may result in a controllable return of articulating segment 426 to a resting state, e.g., unbent or less bent configuration.

In some examples, a shape of distal portion 422 may be preformed. For example, preformed curve segment 430 defines a second curve 431 in a second geometric plane P2. Second geometric plane P2 is illustrated in the plane as least partially out of the page in FIGS. 2A and 2B, and as plane P2 in FIG. 2C. Second geometric plane P2 may be different from first geometric plane P1. For example, first geometric plane P1 and second geometric plane P2 may be offset by an offset angle 427. In some examples, offset angle 427, e.g., the angle of first geometric plane P1 relative to second geometric plane P2, is within a range from about 10 degrees to about 80 degrees, such as about 30 degrees to about 60 degrees or about 40 degree to about 50 degrees.

In some examples, preformed curve segment 430 may be sufficiently flexible to deform into a substantially straight configuration when passed through the vasculature of a patient. Preformed curve segment 430 may be sufficiently resilient to regain the preformed shape of second curve 431 when positioned in the heart of the patient. In some examples, second curve 431 of preformed curve segment 430 may be formed by, for example, heat setting. In some examples, a degree of curvature of preformed curve segment 430 may be in a range between about 10 degrees to about 180 degree, such as between about 30 degrees and about 140 degrees or between about 43.5 degrees and about 124.1 degrees. In some examples, a length of preformed curve segment 430 defining second curve 431 is within a range between about 6 mm and about 10 cm, such as between about 1 cm and about 5 cm or between about 1 cm and about 2 cm. In some examples, a radius 436 of second curve 431 is within a range between about 1 mm and about 20 mm, such as between about 2 mm and about 10 mm. The degree of curvature of preformed curve segment 430 may enable the distal end 425 to be oriented substantially normal to tissue proximate His bundle 3.

In some examples, distal portion 422 may include one or more substantially straight portions. For example, elongate body 420 may include substantially straight portion 428 distal to articulating segment 426 and proximal preformed curve segment 430, and/or substantially straight portion 432 distal to preformed curve segment 430 and including distal end 425. In some examples, a length of substantially straight portion 428 and/or 432 may be in a range between about 1 mm and about 15 mm, such as between about 0.5 mm and about 9 mm.

Distal portion 422 may include at least one radiopaque marker, such as at least one of radiopaque markers 442A, 442B, 442C, and/or 442D (collectively, radiopaque markers 442). Radiopaque markers 442 may include a gold foil, with an adhesive backing, which is sandwiched between layers of distal portion 422, such as any layer of distal portion discussed below in reference to FIG. 3. In some examples, distal portion 422 may include a first radiopaque marker, e.g., radiopaque marker 442A and/or 442B, on articulating segment 426 and a second radiopaque marker, e.g., radiopaque marker 442C and/or 442D, distal to articulating segment 426. In some examples, the second radiopaque marker, e.g., radiopaque marker 442D, may be at least one of on or distal to the preformed curve segment. By positioning radiopaque markers 442 on articulating segment 426 and distal to articulating segment 426, such as at least one of on or distal to the preformed curve segment, a three dimensional position of distal portion 422 may be determined, e.g., observable by a clinician via fluoroscopy.

Articulating segment 426 and preformed curve segment 430 may include any suitable material and construction to achieve flexibility, pushability and torque transfer that facilitates maneuverability of catheter 400 to a target site within the heart of the patient. For example, articulating segment 426 and preformed curve segment 430 may include one or more coaxial layers of polyether block amide, polyurethane, or silicone rubber, or composites thereof.

Figure 3:
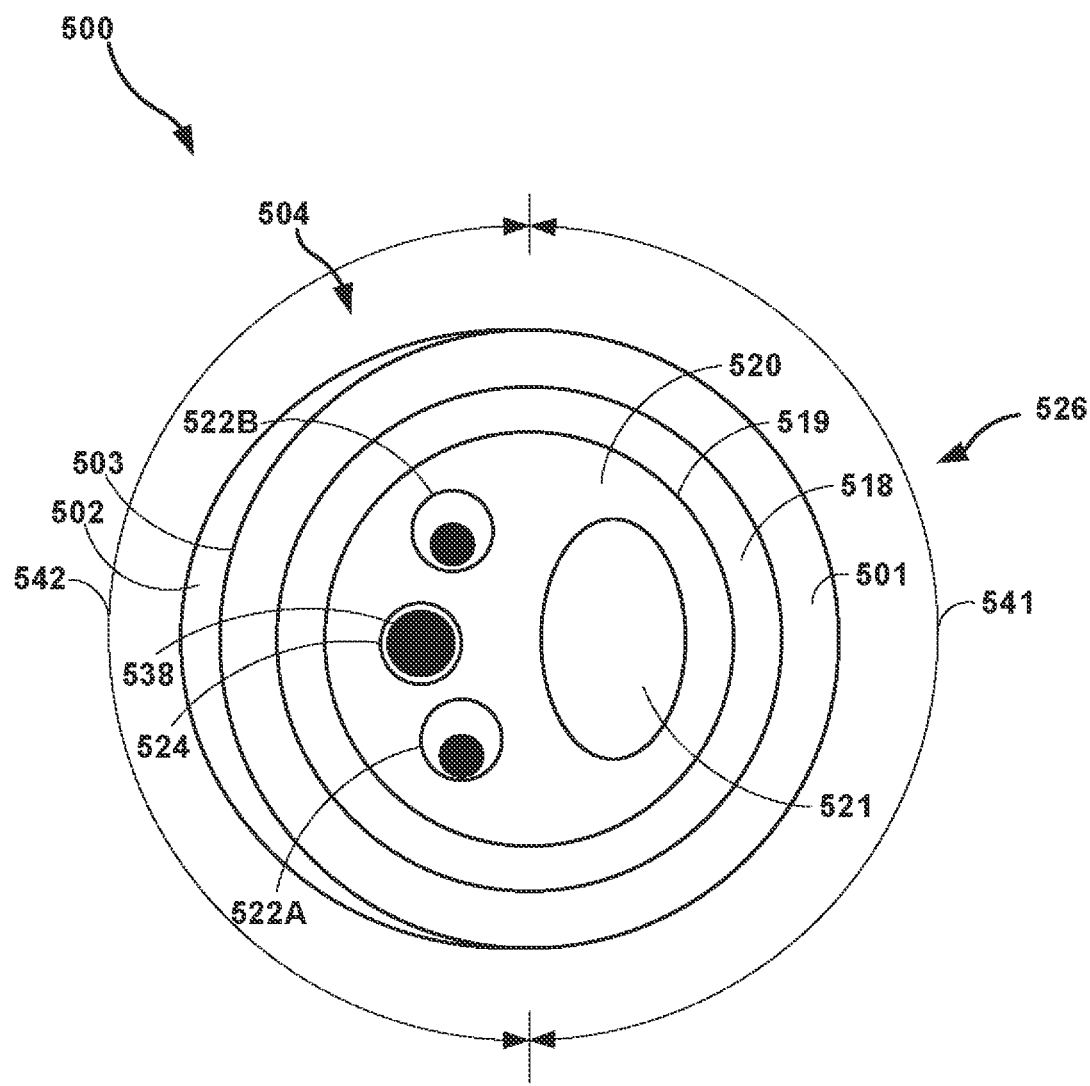
FIG. 3 is a conceptual diagram illustrating a cross-sectional view of an example catheter having an articulating segment including a relatively soft section and relatively stiff section.

FIG. 3 is a conceptual diagram illustrating a cross-sectional view of an example catheter 500 having an articulating segment 526 including a relatively soft section 541 and relatively stiff section 542. Catheter 500, e.g., articulating segment 526, may be the same as or substantially similar to catheter 400, e.g., articulating segment 426, describe above in reference of FIGS. 2A-2C. In some examples, articulating segment 526 may be defined by a composite sidewall 504 that is constructed to bend in one or more curves along one or more geometric planes in response to actuation of pull wire 538. For example, composite sidewall 504 may include a relatively soft section 541 extending longitudinally along a first length of articulating segment 526 and a relatively stiff section 542 extending longitudinally along a second length of articulating segment 526. In some examples, relatively soft section 541 and relatively stiff section 542 may extend along substantially the same length (e.g., the same or nearly the same as limited by catheter manufacturing capabilities) of articulating segment 526, such that the first length and the second length are substantially similar. In other examples, relatively soft section 541 and relatively stiff section 542 may extend along different lengths of distal portion 422, such that at least a portion of the first length of relatively soft section 541 and at least a portion of second length of relatively stiff section 542 overlap along at least a portion of articulating segment 526.

Composite sidewall 504 includes an inner portion 501 and an outer portion 502. Inner portion 501 may extend about 360 degrees around inner assembly 519. Inner portion 501 may include a first polymer having a first durometer. In some examples, inner assembly may include multi-lumen tube 520. Multi-lumen tube 520 includes one, relatively large lumen 521, and three, relatively small lumens 522A, 522B, and 524. Pull wire 538 may extends within lumen 524. Lumens 521, 522A, 522B, and 524 may be fluidly coupled with a distal end 425 of the catheter 400 and a proximal port of handle assembly 410 (FIGS. 2A-2C). In other examples, inner assembly 519 may include a tube having any number of lumens or a single lumen. Outer portion 502 may extend around about 180 degrees of a surface 503 inner portion 501. Outer portion 502 may include a second, different polymer having a second, different durometer (e.g., a higher durometer compared to the first polymer of inner portion 501). In some examples, outer portion 502 may extend around less of inner portion 501 (e.g., at least 10 degrees) or more of inner portion 501 (e.g., up to 350 degrees). Outer portion 502 may be adhered to inner portion 501, such that inner portion 501 forms relatively soft section 541, and the combination of inner portion 501 and outer portion 502 forms relatively stiff section 542. In some examples, composite sidewall 504 may include a reinforcement structure 518. Reinforcement structure 518 may include, for example, a metal braid or metal coil, such as stainless steel or a nickel titanium alloy.

In some examples, when the pull wire 538 is actuated, composite sidewall 504 may cause articulating segment 526 to bend in a first direction in a first geometric plane toward relatively soft section 541, which is more flexible, or provides less resistance to bending than relatively stiff section 542. In other words, a circumferential orientation of relatively soft section 541 and relatively stiff section 542 along a longitudinal axis (e.g., longitudinal axis 402) may be configured to cause articulating segment 526 to controllably bend in a first direction of first curve 429 in response to actuation of pull wire 538 via control member 416. In some examples, an circumferential orientation of relatively soft section 541 and relatively stiff section 542 may be varied along the length of articulating segment 526 to cause articulating segment 526 to controllably bend into complex shapes, including, for example, one or more curves having a plurality of apexes, two or more curve in a single plane, two or more curves in a plurality of planes, or combinations thereof.

Figure 4A:
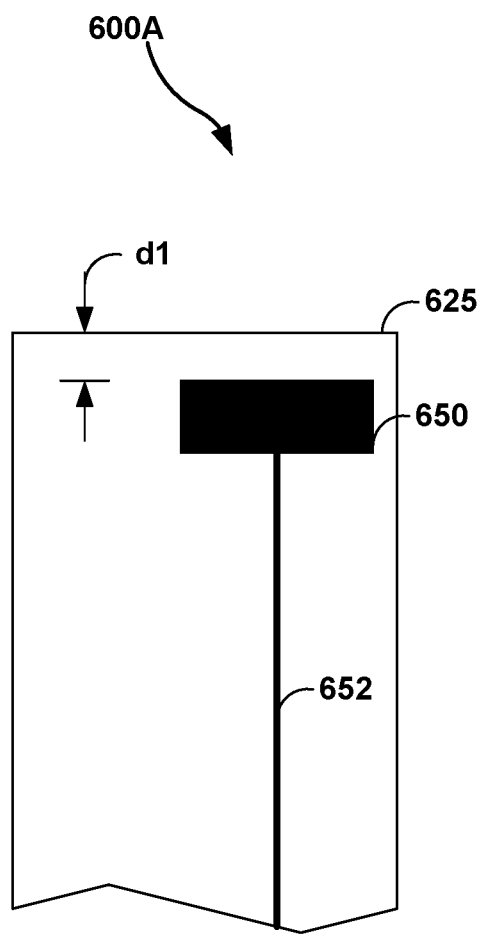
FIGS. 4A and 4B are conceptual diagrams illustrating cross-sectional views of an example catheter including, respectively, a single electrode and a first electrode and a second electrode.
Figure 4B:
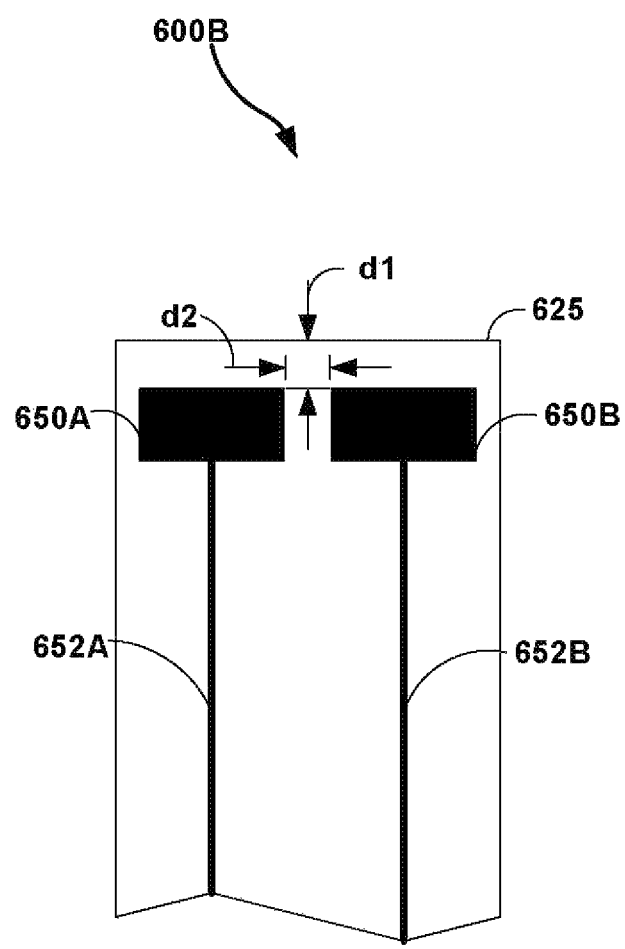

In some examples, catheter 400 may include at least one electrode adjacent to distal end. FIGS. 4A and 4B are a conceptual diagram illustrating cross-sectional views of an example catheters 600A and 600B (collectively, "catheters 600") including, respectively, an electrode array 650 and a first electrode 650A and a second electrode 650B. Electrode array 650 may include one or more electrodes. Catheter 600 is the same as or substantially similar to catheters 400 and/or 500 describe above in reference to FIGS. 2A-3, except for the differences described herein. In the illustrated examples, electrode array 650 (and/or first electrode array 650A and second electrode array 650B) may be formed directly on a component of catheter 600. In other examples, a medical electrical lead (e.g., medical electrical lead 29) may include electrode array 650 (and/or first electrode array 650A and second electrode array 650B) at or near a distal tip of the medical electrical lead, which is introducible through a lumen of catheter 600 (e.g., lumen 521, FIG. 3) to distal end 625.

In the example illustrated in FIG. 4A, electrode array 650 may be electrically coupled to sensing circuitry, e.g., for sensing an electrocardiogram (ECG), to sense a waveform, such as an ECG. For example, catheter 600 may include at least one conductor 652 that electrically couple electrode array 650 to an external device (not shown) configured to receive and condition physiological signals of a patient. In some embodiments, the external device may include a user interface, which may comprise a display for displaying the physiological signals. In some embodiments, the external device may include circuitry, such as digital signal processor (DSP), microprocessor, application specific integrated circuit (ASIC), or other processor or processing circuitry, for processing the signal, e.g., for automatically detecting features in the signal.

Electrode array 650 may be used to determine a target implantation location, such as, for example, a target stimulation location proximate to His bundle 3 (FIGS. 1A and 1B). In some examples, electrode array 650 may include an electrode array, which may be configured to map the focal His bundle. In some examples, the external device or a user, e.g., physician, may detect the location of His bundle 3 based on the ECG waveform. For example, when electrode array 650 is located adjacent His bundle 3, the ECG waveform may include the atrial P-wave, ventricular QRS signature, and a His spike between the P-wave and QRS signature. In examples in which the external device comprises a processor capable of detecting features within a physiological signal, the processor may be capable of detecting an electrical potential waveform indicative of the His bundle 3. For example, the His bundle 3 has a signature waveform with a frequency of about 200 Hz, which may be detectable by the processor. In this way, translating catheter 600 along tissue near His bundle 3 while collecting an ECG may allow determination of a location of His bundle 3.

In some examples, electrode array 650 may be positioned within a lumen of catheter 600, e.g., proximal distal tip 625, to reduce an amplitude of the P-wave and/or QRS signature. For example, electrode array 650 may be positioned a distance d1 from distal tip 625. In some examples, distance d1 may be greater than about 1 mm from distal end 425, such as within a range between about 1 mm and about 2 mm from distal end 425. Reducing the detected amplitude of the P-wave and/or QRS signature may improve detection of the wave of His bundle.

In some examples, the ECG may be used to differentiate between viable tissue suitable for pacing and dead (ischemic) or damaged tissue unsuitable for pacing. For example, the ECG may include a lower voltage amplitude when electrode array 650 are adjacent central fibrous body, dead, or damaged tissue compared to when electrode array 650 are adjacent viable tissue.

In some examples, as illustrated in FIG. 4B, at least one electrode may include a first electrode array 650A and a second electrode array 650B. First electrode array 650A and second electrode array 650B may together define a bipolar electrode pair. In some examples, first electrode array 650A and second electrode array 650B may be arranged at substantially the same longitudinal position, e.g., a distance d1 from distal end 625, with a gap having a distance d2 transverse to the longitudinal axis between them. In some examples, distance d2 may be within a range between about 0.5 mm and about 5 mm. In some examples, conductors 652A and 652B of first electrode array 650A and second electrode array 650B, respectively, may be coupled to an electrical energy source (not shown). For example, the electrical energy source may be part of the external device used for signal monitoring, or a different external device. The electrical energy source may apply a voltage or current between first electrode array 650A and second electrode array 650B. When first electrode array 650A and second electrode array 650B are in contact with tissue or in close proximity to tissue (e.g., less than about 2 mm), the electrical energy from the electrical energy source may travel through the tissue. The current and/or the voltage of the electrical energy traveling through the tissue may be measured, e.g., by the external device, and used to determine an impedance of the tissue. By translating the distal end 625 across the tissue and monitoring the impedance, the location of the His bundle 3 may be determined. For example, tissue including the His bundle 3 may exhibit a lower impedance than an impedance of adjacent endocardial tissue. In some examples, an impedance of tissue of the His bundle 3 may be about 50% lower than an impedance of adjacent endocardial tissue.

Once the target location is determined, a medical electrical lead may be advanced through lumen 421, out distal tip 425, and attached to tissue proximate to the target location, as discussed above.

Electrodes 650, 650A, and 650B may have any shape. For example, electrode array 650 may take the form of a ring of conductive material, or a portion of a ring of conductive material, e.g., not including the full 360 degree circumference of a ring, to, for example, focus sensing in a particular direction transverse to the longitudinal axis may produce a muted response. As another example, each of electrode array 650A and 650B may be a portion (which portions are each less than half of a ring but not necessarily the same circumferential extent) of a ring of conductive material.

Figure 5:
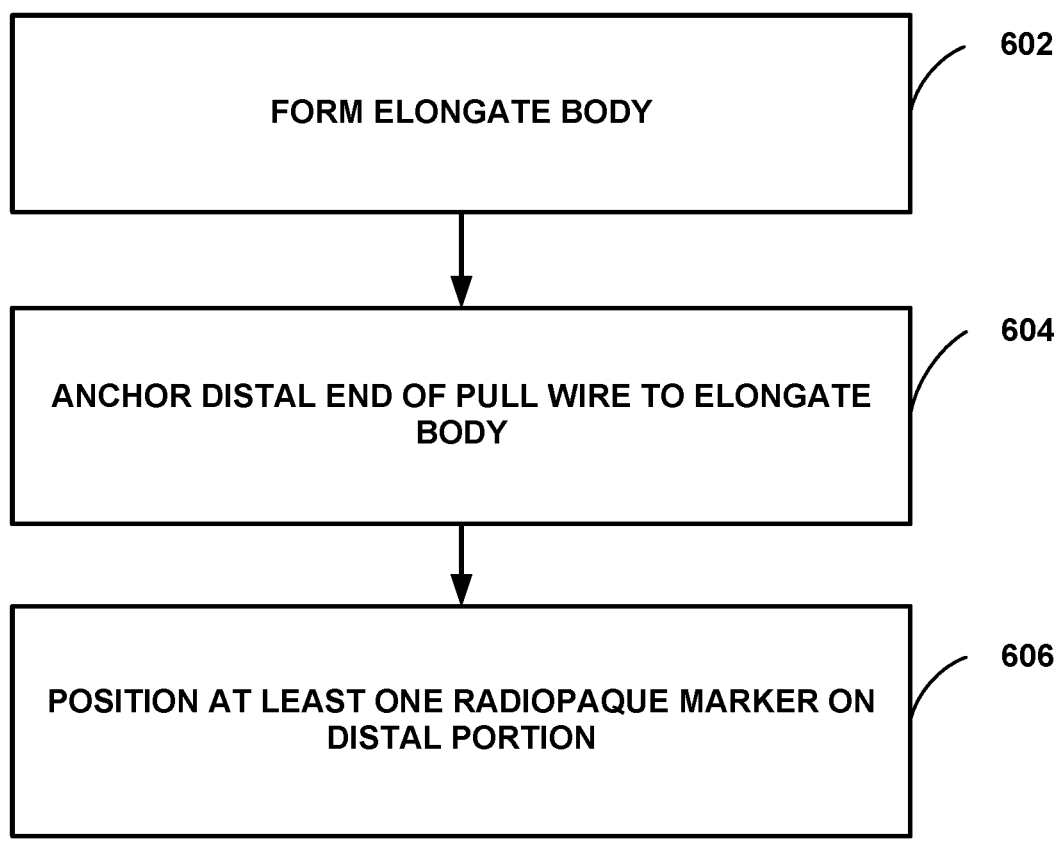
FIG. 5 is a flow diagram illustrating an example method for manufacturing an example catheter.

The catheters describe herein may be used to deliver a medical electrical lead using any suitable technique. FIG. 5 is a flow diagram illustrating an example method for manufacturing an example catheter. The catheter may be the same as or substantially similar to catheters 20, 400, 500, and/or 600 discussed above with respect to FIGS. 1A-4. Although FIG. 5 is described with respect to catheters 400 and 500, in other examples, the method of FIG. 5 may be used with other catheters having features to control the orientation of a distal portion of the catheter, including an articulating segment, a pull wire to controllably bend the articulating segment in a first curve in a first geometric plane, a preformed curve segment defining a second curve in a second geometric plane, at least one radiopaque marker.

The technique illustrated in FIG. 5 includes forming elongate body 420. As discussed above, elongate body 420 may extend from proximal end 423 to distal end 425 and defining lumen 421 extending longitudinally within elongate body 420 (602). Lumen 421 may be configured to receive a medical electrical lead that includes at least one electrode. Elongate body 420 may include proximal portion 424 and distal portion 422. Proximal portion 424 may extend along longitudinal axis 402 and may be configured to couple to handle assembly 410. Distal portion 422 may include an articulating segment 426 and a preformed curve segment 430 distal to articulating segment 426.

Elongate body 420 may be formed by any suitable technique, such as, for example, extrusion of one or more polymers to form inner assembly 519 and deposition of one or more polymer layers on the elongate tube. Two or more elongate tubes may be molded or otherwise adhered together to define a multi-lumen tube 520 of an inner assembly 519. In some examples, forming elongate body 420 may include winding or braiding one or more metal wires onto a mandrel (or inner assembly 519) to form a reinforcement structure (e.g. reinforcement structure 518). In some examples, one or more polymer layers may be deposited on an internal surface and/or external surface of reinforcement structure 518. In some examples, inner assembly 519 may be inserted into reinforcement structure 518.

In some examples, forming elongate body 420 may include forming proximal portion 424, forming distal portion 422, and attaching proximal portion 424 to distal portion 422. Attaching proximal portion 424 to distal portion 422 may include, for example, adhering proximal portion 424 to distal portion 422 using a suitable adhesive or welding (e.g., thermal welding or ultrasonic welding) proximal portion 424 to distal portion 422.

In some examples, forming distal portion 422 may include heat setting (e.g., thermoforming) at least a portion of distal portion 422 to form preformed curve segment 430. In some examples, forming distal portion 422 may include at least forming relatively soft section 541 extending longitudinally along a first length of articulating segment 526 and forming, on at least a portion of a surface of relatively soft section 541, a relatively stiff section 542 extending longitudinally along a second length of articulating segment 526. For example, forming distal portion 422 may include at least forming, e.g., by extrusion or deposition of a polymer on inner assembly 519, inner portion 501 extending longitudinally along the first length of articulating segment 526. As discussed above, inner portion 501 extend about 360 degrees around inner assembly 519 and may include a first polymer having a first durometer. Forming distal portion 422 also may include forming, e.g., by extrusion or deposition of a polymer on inner assembly 519, on at least a portion of surface 503 of inner portion 501, outer portion 502 extending longitudinally along a second length of the articulating segment. As discussed above, outer portion 502 may extend around about 180 degrees of surface 503 inner portion 501 and may include a second, different polymer having a second, different durometer.

The technique illustrated in FIG. 5 also includes anchoring distal end 439 of pull wire 438 to elongate body 420 (604). As discussed above, pull wire 438 may extend from control member 416 of handle assembly 410 to distal end 439 such that pull wire 438, by actuation of control member 416, may be configured to controllably bend articulating segment 426 in a first curve in first geometric plane P1. In some examples, anchoring distal end 439 to elongate body 420 may include adhering or otherwise affixing distal end 439 to a portion of elongate body 420, such as a portion of lumen 524.

The technique illustrated in FIG. 5 also includes positioning at least one radiopaque marker on the distal portion (606). In some examples, positioning at least one radiopaque marker may include adhering a radiopaque material, such as gold foil, between layers of distal portion 422, such as between inner assembly 519 and inner portion 501.

Figure 6:
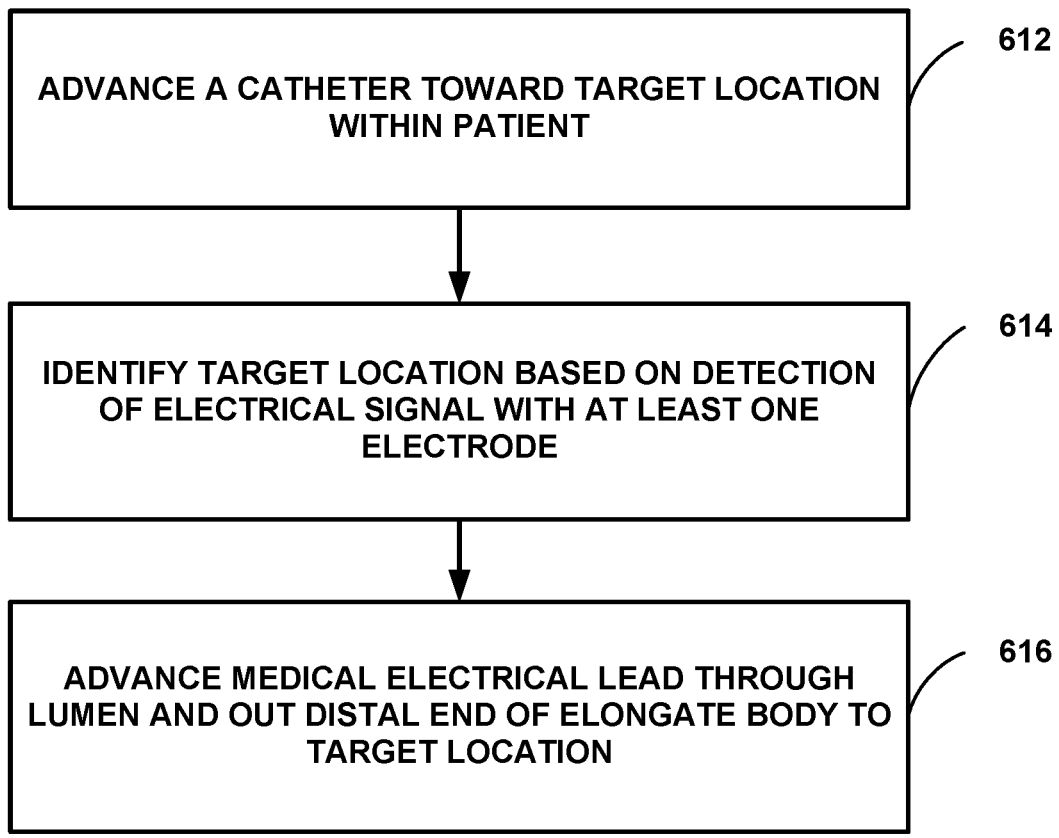
FIG. 6 is a flow diagram illustrating an example method of delivering a medical electrical lead to a target location using an example catheter.

The catheters described herein may be assembled using any suitable technique. FIG. 6 is a flow diagram illustrating an example method of delivering a medical electrical lead to a target location using an example catheter. The catheter may be the same as or substantially similar to catheters 20, 400, 500, and/or 600 discussed above with respect to FIGS. 1A-3. Although FIG. 6 is described with respect to catheters 20, 400, and 500, in other examples, the method of FIG. 6 may be used to assemble other catheters having features configured to control the orientation of a distal portion of the catheter, including an articulating segment, a pull wire to controllably bend the articulating segment in a first curve in a first geometric plane, a preformed curve segment defining a second curve in a second geometric plane, at least one radiopaque marker.

The technique illustrated in FIG. 6 includes advancing catheter 400, as discussed above, toward a target location (e.g., His bundle 3) within a patient (612). In examples in which catheter 400 includes a first radiopaque marker (e.g., radiopaque marker 442A or 442B) on articulating segment 426 and a second radiopaque marker (e.g., radiopaque marker 442C or 442D) distal to articulating segment 426, advancing catheter 400 toward the target location, may include imaging the first radiopaque marker and the second radiopaque marker to determine, based on a position of the first radiopaque marker and the second radiopaque marker, a three dimensional configuration of distal portion 422. In some examples, after advancing catheter 400 toward the target location, the technique may include actuating control member 416, e.g., via one or more controls 418, to cause pull wire 438 to controllably bend articulating segment 426 into first curve 429.

The technique illustrated in FIG. 6 also includes identifying the target location based on the detection of the electrical signal with at least one electrode 450 (614). For example, as discussed above, electrode 450 may be electrically coupled to sensing circuitry by electrical coupling 452, e.g., for sensing an electrocardiogram (ECG), to enable an external device or a user to detect the location of His bundle 3. In this way, the technique may include translating catheter 400 along tissue near His bundle 3 while collecting an ECG may allow determination of a location of His bundle 3. In some examples, the technique may include controlling a position of electrode 450 relative to distal end 425 to reduce an amplitude of the P-wave and/or QRS signature, as discussed above, to improve detection of the His spike.

In some examples, the technique may include measuring a current and/or a voltage to determine an impedance of tissue between a first electrode and a second electrode adjacent to and separated a distance from the first electrode (e.g., a bipolar electrode). For example, the technique may include translating the medical electrical lead 29 across the tissue and monitoring the impedance of the tissue to identify an impedance indicative of His bundle 3.

The technique illustrated in FIG. 6 also includes, after identifying the target location, advancing the medical electrical lead 29 through lumen 421 and out distal end 425 of elongate body 420 to the target location (616). For example, the technique may include advancing medical electrical lead 29 out of distal end 425 of catheter 400 and controlling lead helix 30, e.g., via a lead body of medical electrical lead 29 controllable at or near a handle assembly of catheter 20, to screw distal helix 30 into the tissue proximate His bundle 3.

The following clauses illustrate example subject matter described herein.

Clause 1. A catheter comprising: a handle assembly having a control member; an elongate body extending from a proximal end to a distal end and defining a lumen extending longitudinally within the elongate body, the lumen configured to receive a medical electrical lead comprising at least one electrode, wherein the elongate body comprises: a proximal portion coupled to the handle assembly and extending along a longitudinal axis; and a distal portion comprising: an articulating segment; and a preformed curve segment distal the articulating segment; a pull wire extending from the control member and anchored to the elongate body distal to the articulating segment; and at least one radiopaque marker, wherein the pull wire, by actuation of the control member, is configured to controllably bend the articulating segment in a first curve in a first geometric plane, and wherein the preformed curve segment defines a second curve in a second geometric plane different from the first geometric plane, wherein the at least one radiopaque marker is positioned on the second curve.

Clause 2. The catheter of clause 1, wherein the catheter further comprises at least one electrode array adjacent to the distal end.

Clause 3. The catheter of clause 2, wherein the at least one electrode array is positioned greater than about 1 millimeter from the distal end of the elongate body.

Clause 4. The catheter of clause 2, wherein the at least one electrode array is positioned between about 1 millimeter and about 2 millimeters from the distal end of the elongate body.

Clause 5. The catheter of any one of clauses 2 through 4, wherein the at least one electrode array comprises a first electrode and a second electrode, wherein the first and second electrodes are arranged at substantially the same longitudinal position with a gap transverse to the longitudinal axis between them.

Clause 6. The catheter of any one of clauses 1 through 5, wherein a length of the articulating segment defining the first curve is within a range from about 5 centimeters (cm) to about 20 cm.

Clause 7. The catheter of any one of clauses 1 through 6, wherein a length of the preformed curve segment defining the second curve is within a range from about 2 cm and about 5 cm.

Clause 8. The catheter of any one of clauses 1 through 7, wherein a radius of the first curve is within a range from about 5 mm and about 30 mm.

Clause 9. The catheter of any one of clauses 1 through 8, wherein a radius of the second curve is within a range from about 1 mm and about 20 mm.

Clause 10. The catheter of any one of clauses 1 through 9, wherein an angle of the first curve is within a range from about 10 degrees and about 240 degrees.

Clause 11. The catheter of any one of clauses 1 through 10, wherein an angle of the second curve is within a range from about 10 degrees and about 180 degrees.

Clause 12. The catheter of any one of clauses 1 through 11, wherein an offset of the first geometric plane relative to the second geometric plane is within a range from about 10 degrees to about 80 degrees.

Clause 13. The catheter of any one of clauses 1 through 12, wherein the elongate body comprises a substantially straight portion distal to the preformed curve segment and including the distal end, wherein a length of the substantially straight portion is between about 5 mm and about 9 mm.

Clause 14. The catheter of any one of clauses 1 through 13, wherein the articulating segment is defined by a composite sidewall comprising: a relatively soft section extending longitudinally along a first length of the articulating segment; and a relatively stiff section extending longitudinally along a second length of the articulating segment.

Clause 15. The catheter of clause 14, wherein a circumferential orientation of the relatively soft section and the relatively stiff section along the longitudinal axis is configured to cause the articulating segment to controllably bend in a first direction of the first curve in response to actuation of the pull wire via the control member.

Clause 16. The catheter of any one of clauses 1 through 15, wherein the at least one radiopaque marker comprises: a first radiopaque marker on the articulating segment; and a second radiopaque marker distal to the articulating segment.

Clause 17. The catheter of clause 16, wherein the second radiopaque marker is at least one of on or distal to the preformed curve segment.

Clause 18. A delivery catheter comprising: a handle assembly having a control member; an elongate body extending from a proximal end to a distal end and defining a lumen extending longitudinally within the elongate body, the lumen configured to receive the medical electrical lead, wherein the elongate body comprises: a proximal portion coupled to the handle assembly and extending along a longitudinal axis; and a distal portion comprising: an articulating segment; and a preformed curve segment distal the articulating segment, a pull wire extending from the control member and anchored to the elongate body distal to the articulating segment; at least one electrode array configured to sense an electrical signal indicative of a His bundle of a heart of a patient; a first radiopaque marker on the articulating segment; and a second radiopaque marker distal to the articulating segment; wherein the pull wire, by actuation of the control member, is configured to controllably bend the articulating segment in a first curve in a first geometric plane, and wherein the preformed curve segment defines a second curve in a second geometric plane different from the first geometric plane, and wherein an offset of the first geometric plane relative to the second geometric plane is within a range from about 40 degrees to about 50 degrees.

Clause 19. A kit comprising: a catheter comprising: a handle assembly having a control member; an elongate body extending from a proximal end to a distal end and defining a lumen extending longitudinally within the elongate body, wherein the elongate body comprises: a proximal portion coupled to the handle assembly and extending along a longitudinal axis; and a distal portion comprising: an articulating segment; and a preformed curve segment distal the articulating segment, a pull wire extending from the control member and anchored to the elongate body distal to the articulating segment; and at least one radiopaque marker positioned on the distal portion, wherein the pull wire, by actuation of the control member, is configured to controllably bend the articulating segment in a first curve in a first geometric plane, and wherein the preformed curve segment defines a second curve in a second geometric plane different from the first geometric plane; and an implantable element for at least one of therapy delivery or sensing that is sized for delivery through the lumen and out of the distal end of the elongate body.

Clause 20. The kit of clause 19, wherein the catheter further comprises at least one electrode array adjacent to the distal end.

Clause 21. The kit of clause 20, wherein the at least one electrode array is positioned greater than about 1 millimeter from the distal end of the elongate body.

Clause 22. The kit of any one of clauses 19 through 21, wherein an angle of the first curve is within a range from about 10 degrees and about 240 degrees.

Clause 23. The kit of any one of clauses 19 through 22, wherein an angle of the second curve is within a range from about 10 degrees and about 180 degrees.

Clause 24. The kit of any one of clauses 19 through 23, wherein an offset of the first geometric plane relative to the second geometric plane is within a range from about 10 degrees to about 80 degrees.

Clause 25. The kit of any one of clauses 19 through 24, wherein the articulating segment is defined by a composite sidewall comprising: a relatively soft section extending longitudinally along a first length of the articulating segment; and a relatively stiff section extending longitudinally along the length of the articulating segment.

Clause 26. The kit of clause 25, wherein an circumferential orientation of the relatively soft section and the relatively stiff section along the longitudinal axis is configured to cause the articulating segment to controllably bend in a first direction of the first curve in response to actuation of the pull wire via the control member.

Clause 27. The kit of any one of clauses 19 through 26, wherein the at least one radiopaque marker comprises: a first radiopaque marker adjacent the articulating segment; and a second radiopaque marker adjacent the distal end.

Clause 28. The kit of any one of clauses 19 through 26, wherein the at least one radiopaque marker comprises: a first radiopaque marker adjacent the articulating segment; and a second radiopaque marker adjacent the preformed curve segment.

Clause 29. A method comprising: advancing a catheter toward a target location within a patient, wherein the catheter comprises: at least one electrode array configured to detect an electrical signal indicative of the His bundle of a heart of the patient; a handle assembly having a control member; an elongate body extending from a proximal end to a distal end and defining a lumen extending longitudinally within the elongate body, the lumen configured to receive a medical electrical lead, wherein the elongate body comprises: proximal portion coupled to the handle assembly and extending along a longitudinal axis; and a distal portion comprising: an articulating segment; and a preformed curve segment distal the articulating segment, a pull wire extending from the control member and anchored to the elongate body distal to the articulating segment; and at least one radiopaque marker positioned on the distal portion, wherein the pull wire, by actuation of the control member, is configured to controllably bend the articulating segment in a first curve in a first geometric plane, and wherein the preformed curve segment defines a second curve in a second geometric plane different from the first geometric plane, identifying the target location based on the detection of the electrical signal with the at least one electrode array; and advancing a medical electrical lead through the lumen and out the distal end of the elongate body to the target location.

Clause 30. The method of clause 29, wherein the method further comprises, after advancing the catheter toward the target location, actuating the control member to cause the pull wire to controllably bend the articulating segment into the first curve.

Clause 37. The method of any one of clauses 29 through 36, wherein the at least one radiopaque marker comprises: a first radiopaque marker on the articulating segment; and a second radiopaque marker distal to the articulating segment, and wherein the method further comprises, after advancing the catheter toward the target location, imaging the first radiopaque marker and the second radiopaque marker to determine, based on a position of the first radiopaque marker and the second radiopaque marker, a three dimensional configuration of the distal portion.

Clause 38. The method of any one of clauses 29 through 36, wherein the at least one radiopaque marker comprises: a first radiopaque marker adjacent the articulating segment; and a second radiopaque marker adjacent the preformed curve segment, and wherein advancing the catheter toward the target location comprises imaging the first radiopaque marker and the second radiopaque marker to determine, based on a position of the first radiopaque marker and the second radiopaque marker, a three dimensional configuration of the distal portion.

Clause 33. A method comprising: forming an elongate body extending from a proximal end to a distal end and defining a lumen extending longitudinally within the elongate body, the lumen configured to receive a medical electrical lead comprising at least one electrode array, wherein the elongate body comprises: a proximal portion coupled to the handle assembly and extending along a longitudinal axis; and a distal portion comprising: an articulating segment; and a preformed curve segment distal the articulating segment anchoring a distal end of a pull wire to the elongate body, wherein the pull wire extends from a control member of a handle assembly to the distal end, wherein the pull wire, by actuation of the control member, is configured to controllably bend the articulating segment in a first curve in a first geometric plane; positioning at least one radiopaque marker on the distal portion, wherein the preformed curve segment defines a second curve in a second geometric plane different from the first geometric plane.

Clause 34. The method of clause 33, wherein forming the elongate body comprises: forming the proximal portion; and forming the distal portion by at least: forming an inner portion extending longitudinally along a first length of the articulating segment; and forming, on at least a portion of a surface of the inner portion, an outer portion extending longitudinally along a second length of the articulating segment; and attaching the proximal portion to the distal portion.

Clause 35. The method of clause 33 or 34, wherein forming the distal portion comprises controlling a circumferential orientation of the relatively soft section and the relatively stiff section along the longitudinal axis, wherein the circumferential orientation of the relatively soft section and the relatively stiff section is configured to cause the articulating segment to controllably bend in a first direction of the first curve in response to actuation of the pull wire via the control member.

Various examples of the disclosure have been described. Any combination of the described systems, operations, or functions is contemplated. These and other examples are within the scope of the following claims.

What is claimed is:

1. A catheter comprising:
    a handle assembly comprising:
        an adjustable handle; and
        a control member;
    an elongate body extending from a proximal end to a distal end and defining a lumen extending longitudinally within the elongate body, the lumen configured to receive a medical electrical lead comprising at least one electrode, wherein the elongate body comprises:
        a proximal portion coupled to the handle assembly and extending along a longitudinal axis; and
        a distal portion comprising:
            an articulating segment; and
            a preformed curve segment distal the articulating segment,
            wherein the adjustable handle is configured to manipulate a deflection of the distal portion;
    a pull wire extending from the control member and anchored to the elongate body distal to the articulating segment;
    at least one electrode array, positioned within the lumen, comprising a first electrode and a second electrode, the first electrode and the second electrode at substantially the same longitudinal position greater than about 1 millimeter (mm) proximal from the distal end with a gap transverse to the longitudinal axis between them; and
    at least one radiopaque marker,
    wherein the pull wire, by actuation of the control member, is configured to controllably bend the articulating segment in a first curve in a first geometric plane, and
    wherein the preformed curve segment defines a second curve in a second geometric plane different from the first geometric plane, wherein the at least one radiopaque marker is positioned on the second curve.

2. The catheter of claim 1, wherein the at least one electrode array is positioned between about 1 mm and about 2 mm from the distal end of the elongate body.

3. The catheter of claim 1, wherein a length of the articulating segment defining the first curve is within a range from about 5 centimeters (cm) to about 20 cm.

4. The catheter of claim 1, wherein a length of the preformed curve segment defining the second curve is within a range from about 2 cm and about 5 cm.

5. The catheter of claim 1, wherein a radius of the first curve is within a range from about 5 mm and about 30 mm.

6. The catheter of claim 1, wherein a radius of the second curve is within a range from about 1 mm and about 20 mm.

7. The catheter of claim 1, wherein an angle of the first curve is within a range from about 10 degrees and about 240 degrees.

8. The catheter of claim 1, wherein an angle of the second curve is within a range from about 10 degrees and about 180 degrees.

9. The catheter of claim 1, wherein an offset of the first geometric plane relative to the second geometric plane is within a range from about 10 degrees to about 80 degrees.

10. The catheter of claim 1, wherein the elongate body comprises a substantially straight portion distal to the preformed curve segment and including the distal end, wherein a length of the substantially straight portion is between about 5 mm and about 9 mm.

11. The catheter of claim 1, wherein the articulating segment is defined by a composite sidewall comprising:
    a relatively soft section extending longitudinally along a first length of the articulating segment; and
    a relatively stiff section extending longitudinally along a second length of the articulating segment.

12. The catheter of claim 11, wherein a circumferential orientation of the relatively soft section and the relatively stiff section along the longitudinal axis is configured to cause the articulating segment to controllably bend in a first direction of the first curve in response to actuation of the pull wire via the control member.

13. The catheter of claim 1, wherein the catheter further comprises a second radiopaque marker on the articulating segment.

14. The catheter of claim 1, wherein the catheter further comprises a second radiopaque marker at least one of on or distal to the preformed curve segment.

15. The catheter of claim 1, wherein the at least one electrode array is configured to detect an impedance of a tissue at the distal end of the elongate body.

16. The catheter of claim 1, wherein the adjustable handle is configured to manipulate the deflection of the distal portion by rotating the deflection of the distal portion.

17. A delivery catheter comprising:
    a handle assembly comprising:
        an adjustable handle; and
        a control member;
    an elongate body extending from a proximal end to a distal end and defining a lumen extending longitudinally within the elongate body, the lumen configured to receive a medical electrical lead, wherein the elongate body comprises:
        a proximal portion coupled to the handle assembly and extending along a longitudinal axis; and
        a distal portion comprising:
            an articulating segment; and a preformed curve segment distal the articulating segment,
wherein the adjustable handle is configured to manipulate a deflection of the distal portion;
a pull wire extending from the control member and anchored to the elongate body distal to the articulating segment;
at least one electrode array, positioned within the lumen, comprising a first electrode and a second electrode, the first electrode and the second electrode at substantially the same longitudinal position greater than about 1 millimeter (mm) proximal from the distal end with a gap transverse to the longitudinal axis between them, wherein the at least one electrode array is configured to sense an electrical signal indicative of a His bundle of a heart of a patient;
a first radiopaque marker on the articulating segment; and
a second radiopaque marker distal to the articulating segment;
wherein the pull wire, by actuation of the control member, is configured to controllably bend the articulating segment in a first curve in a first geometric plane, and
wherein the preformed curve segment defines a second curve in a second geometric plane different from the first geometric plane, and
wherein an offset of the first geometric plane relative to the second geometric plane is within a range from about 40 degrees to about 50 degrees.

18. The delivery catheter of claim 17, wherein the at least one electrode array is configured to detect an impedance of a tissue at the distal end of the elongate body.

19. The delivery catheter of claim 17, wherein the adjustable handle is configured to manipulate the deflection of the distal portion by rotating the deflection of the distal portion.

20. A kit comprising:
a catheter comprising:
a handle assembly comprising:
an adjustable handle; and
a control member;
an elongate body extending from a proximal end to a distal end and defining a lumen extending longitudinally within the elongate body, wherein the elongate body comprises:
a proximal portion coupled to the handle assembly and extending along a longitudinal axis; and
a distal portion comprising:
an articulating segment; and
a preformed curve segment distal the articulating segment,
wherein the adjustable handle is configured to manipulate a deflection of the distal portion;
a pull wire extending from the control member and anchored to the elongate body distal to the articulating segment;
at least one electrode array, positioned within the lumen, comprising a first electrode and a second electrode, the first electrode and the second electrode at substantially the same longitudinal position greater than about 1 millimeter (mm) proximal from the distal end with a gap transverse to the longitudinal axis between them; and
at least one radiopaque marker positioned on the distal portion,
wherein the pull wire, by actuation of the control member, is configured to controllably bend the articulating segment in a first curve in a first geometric plane, and
wherein the preformed curve segment defines a second curve in a second geometric plane different from the first geometric plane;
and
an implantable element for at least one of therapy delivery or sensing that is sized for delivery through the lumen and out of the distal end of the elongate body.

21. The kit of claim 20, wherein an angle of the first curve is within a range from about 10 degrees and about 240 degrees.

22. The kit of claim 20, wherein an angle of the second curve is within a range from about 10 degrees and about 180 degrees.

23. The kit of claim 20, wherein an offset of the first geometric plane relative to the second geometric plane is within a range from about 10 degrees to about 80 degrees.

24. The kit of claim 20, wherein the articulating segment is defined by a composite sidewall comprising:
a relatively soft section extending longitudinally along a first length of the articulating segment; and
a relatively stiff section extending longitudinally along a second length of the articulating segment.

25. The kit of claim 24, wherein a circumferential orientation of the relatively soft section and the relatively stiff section along the longitudinal axis is configured to cause the articulating segment to controllably bend in a first direction of the first curve in response to actuation of the pull wire via the control member.

26. The kit of claim 20, wherein the at least one radiopaque marker comprises:
a first radiopaque marker adjacent the articulating segment; and
a second radiopaque marker adjacent the distal end.

27. The kit of claim 20, wherein the at least one radiopaque marker comprises:
a first radiopaque marker adjacent the articulating segment; and
a second radiopaque marker adjacent the preformed curve segment.

28. The kit of claim 20, wherein the at least one electrode array is configured to detect an impedance of a tissue at the distal end of the elongate body.

29. The kit of claim 20, wherein the adjustable handle is configured to manipulate the deflection of the distal portion by rotating the deflection of the distal portion.

* * * * *